United States Patent
Lader (10) Patent No.: US 8,367,320 B2
(45) Date of Patent: Feb. 5, 2013

(54) APOPTOSIS INDUCING POSITIVE CONTROL FOR EXPRESSION MODULATION EXPERIMENTS

(75) Inventor: Eric Lader, Boyds, MD (US)

(73) Assignee: Qiagen Sciences, Inc., Germantown, MD (US)

( * ) Notice: Subject to any disclaimer, the term of this patent is extended or adjusted under 35 U.S.C. 154(b) by 75 days.

(21) Appl. No.: 12/810,281

(22) PCT Filed: Dec. 29, 2008

(86) PCT No.: PCT/IB2008/003644
§ 371 (c)(1),
(2), (4) Date: Jun. 23, 2010

(87) PCT Pub. No.: WO2009/083790
PCT Pub. Date: Jul. 9, 2009

(65) Prior Publication Data
US 2010/0285484 A1    Nov. 11, 2010

Related U.S. Application Data

(60) Provisional application No. 61/017,328, filed on Dec. 28, 2007.

(51) Int. Cl.
*C12Q 1/68* (2006.01)

(52) U.S. Cl. ............... 435/6; 435/325; 435/375; 514/44

(58) Field of Classification Search ........................ None
See application file for complete search history.

(56) References Cited

U.S. PATENT DOCUMENTS
2011/0034535 A1 *  2/2011  Hahn et al. ................. 514/44 A FOREIGN PATENT DOCUMENTS
WO    WO2005014811       *  2/2005
WO    2005/047477 A2       5/2005

OTHER PUBLICATIONS

Tchurikov, N.A.; "Molecular Mechanisms of Epigenetics"; Biochemistry (Moscow); Kluwer Academic Publications—Plenum Publishers, NE; vol. 70, No. 4; Apr. 1, 2005; pp. 406-423 (XP019294587).
Fedorov, Yuriy et al.; "Off-target effects by siRNA can induce toxic phenotype"; RNA (Cold Spring Harbor); vol. 12, No. 7; Jul. 2006; pp. 1188-1195 (XP002547706).

\* cited by examiner

*Primary Examiner* — Kimberly Chong
(74) *Attorney, Agent, or Firm* — Rankin, Hill & Clark LLP (57) ABSTRACT

The invention pertains to a method for performing an expression modulating analysis or assay, wherein an apoptosis inducing expression modulating compound targeting a repetitive element present in the untranslated region, in particular the 3' UTRs of protein coding gene transcripts is introduced into cells to induce apoptosis in the cells as a positive control. Also provided are suitable kits and compositions.

23 Claims, 4 Drawing Sheets

SEQUENCE LISTING

<160> NUMBER OF SEQ ID NOS: 30

<210> SEQ ID NO 1
<211> LENGTH: 21
<212> TYPE: DNA
<213> ORGANISM: Homo sapiens

<400> SEQUENCE: 1
cctcccaaag tgctgggatt a                                              21

<210> SEQ ID NO 2
<211> LENGTH: 21
<212> TYPE: DNA
<213> ORGANISM: Homo sapiens

<400> SEQUENCE: 2
cacctgtaat cccagcactt t                                              21

<210> SEQ ID NO 3
<211> LENGTH: 21
<212> TYPE: DNA
<213> ORGANISM: Homo sapiens

<400> SEQUENCE: 3
ctggaggctg aggcaggaga a                                              21

<210> SEQ ID NO 4
<211> LENGTH: 21
<212> TYPE: DNA
<213> ORGANISM: Homo sapiens

<400> SEQUENCE: 4
aagcctgtaa tcccagcact t                                              21

<210> SEQ ID NO 5
<211> LENGTH: 18
<212> TYPE: DNA
<213> ORGANISM: Homo sapiens

<400> SEQUENCE: 5
cctgtaatcc cagcactt                                                  18

<210> SEQ ID NO 6
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 6
caggcggatt tctgagttcg a                                              21

<210> SEQ ID NO 7
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 7
agccagggct acacagagaa a                                              21

-continued

<210> SEQ ID NO 8
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 8
cagaggcagg cggatttctg a                                            21

<210> SEQ ID NO 9
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 9
catggtggcg cacgccttta a                                            21

<210> SEQ ID NO 10
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 10
aaggccaaga tccaggataa a                                            21

<210> SEQ ID NO 11
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 11
aagtttagaa attacaagtt t                                            21

<210> SEQ ID NO 12
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 12
cggcaagacc atcaccctgg a                                            21

<210> SEQ ID NO 13
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 13
cgtgaagacc ctgaccggca a                                            21

<210> SEQ ID NO 14

```
<211> LENGTH: 21
<212> TYPE: DNA
<213> ORGANISM: Artificial Sequence
<220> FEATURE:
<223> OTHER INFORMATION: Target sequence of Ubiquitin specific for human
      Ubiquitin

<400> SEQUENCE: 14
cctgttcaaa atgttaataa a                                              21

<210> SEQ ID NO 15
<211> LENGTH: 21
<212> TYPE: DNA
<213> ORGANISM: Artificial Sequence
<220> FEATURE:
<223> OTHER INFORMATION: Target sequence of Ubiquitin specific for human
      Ubiquitin

<400> SEQUENCE: 15
aaggccaaga tccaagataa a                                              21

<210> SEQ ID NO 16
<211> LENGTH: 21
<212> TYPE: DNA
<213> ORGANISM: Artificial Sequence
<220> FEATURE:
<223> OTHER INFORMATION: Target sequence of Ubiquitin specific for human
      Ubiquitin

<400> SEQUENCE: 16
caggatcctg gtatccgcta a                                              21

<210> SEQ ID NO 17
<211> LENGTH: 21
<212> TYPE: DNA
<213> ORGANISM: Artificial Sequence
<220> FEATURE:
<223> OTHER INFORMATION: Target sequence of Ubiquitin specific for human
      Ubiquitin

<400> SEQUENCE: 17
ccaacttaag tttagaaatt a                                              21

<210> SEQ ID NO 18
<211> LENGTH: 21
<212> TYPE: DNA
<213> ORGANISM: Artificial Sequence
<220> FEATURE:
<223> OTHER INFORMATION: Target sequence of plk1 specific for human,
      mouse and rat

<400> SEQUENCE: 18
cagtattccc aagcacatca a                                              21

<210> SEQ ID NO 19
<211> LENGTH: 21
<212> TYPE: DNA
<213> ORGANISM: Artificial Sequence
<220> FEATURE:
<223> OTHER INFORMATION: Target sequence of plk1 specific for human,
      mouse and rat

<400> SEQUENCE: 19
ccgcagcgcc atcatcctgc a                                              21

<210> SEQ ID NO 20
<211> LENGTH: 21
<212> TYPE: DNA
```

```
<213> ORGANISM: Artificial Sequence
<220> FEATURE:
<223> OTHER INFORMATION: Target sequence of plk1 specific for human,
      mouse and rat

<400> SEQUENCE: 20
ccggaggtcc tagtggaccc a                                            21

<210> SEQ ID NO 21
<211> LENGTH: 21
<212> TYPE: DNA
<213> ORGANISM: Artificial Sequence
<220> FEATURE:
<223> OTHER INFORMATION: Target sequence of plk1 specific for human,
      mouse and rat

<400> SEQUENCE: 21
cctgcagtac atagagcgtg a                                            21

<210> SEQ ID NO 22
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 22
caccatatga attgtacaga a                                            21

<210> SEQ ID NO 23
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 23
aaccattaac gagctgctta a                                            21

<210> SEQ ID NO 24
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 24
taaacagatg tgaatattca a                                            21

<210> SEQ ID NO 25
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 25
aagaagatca ccctccttaa a                                            21

<210> SEQ ID NO 26
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 26
```

```
ctgccagtac ctgcaccgaa a                                              21

<210> SEQ ID NO 27
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 27
cacattaaac agatgtgaat a                                              21

<210> SEQ ID NO 28
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 28
caaggaggtg ttcgcgggca a                                              21

<210> SEQ ID NO 29
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 29
caacggcagc gtgcagatca a                                              21

<210> SEQ ID NO 30
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 30
cagcgtgcag atcaacttct t                                              21
```

APOPTOSIS INDUCING POSITIVE CONTROL FOR EXPRESSION MODULATION EXPERIMENTS

The present invention pertains to the use of certain expression modulating compounds as positive controls in assay systems as well as to the respective expression modulating compounds.

Many methods are known in the state of the art that target and/or influence gene expression. Earlier methods modified the DNA, e.g. by mutation or recombination. Such methods, however, altered the genetic identity of the organism.

Several new techniques were established in the last years that did not target the DNA but the RNA (mRNA) in order to alter/modulate gene expression. These RNA-targeting techniques allow modulation of gene expression such that only minimal levels of functional mRNA remain, thereby allowing even the regulation of essential genes. These techniques allow the creation of specific phenotypes as well as the analysis of the gene function in different developmental stages.

One of the earlier methods of these RNA-targeting techniques was the antisense technology. Antisense polynucleotides are designed to specifically bind to RNA, resulting in the formation of RNA-DNA or RNA-RNA hybrids, with an arrest of reverse transcription or messenger RNA translation. Antisense polynucleotides based on a selected sequence can thus modulate the expression of the corresponding gene as the mRNA is targeted and e.g. translation is at least partially inhibited. Many forms of antisense have been developed and can be broadly categorized into enzyme-dependent antisense or steric blocking antisense. Enzyme-dependent antisense includes forms dependent on RNase H activity to degrade target mRNA, including single-stranded DNA, RNA, and phosphorothioate antisense.

Antisense polynucleotides are typically generated within the cell by expression from antisense constructs that contain the antisense strand as the transcribed strand. Antisense polynucleotides will bind and/or interfere with the translation of the corresponding mRNA. As such, antisense may be used for research purposes as well as therapeutically e.g. to inhibit the expression of oncogenes.

Antisense RNA or antisense oligodeoxynucleotides (antisense ODNs) can both be used and may also be prepared in vitro synthetically or by means of recombinant DNA techniques. Both methods are well within the reach of the person skilled in the art. ODNs are smaller than complete antisense RNAs and have therefore the advantage that they can more easily enter the target cell. In order to avoid their digestion by DNAse, ODNs and antisense RNAs may be chemically modified.

Trans-cleaving catalytic RNAs (ribozymes) are RNA molecules possessing endoribo-nuclease activity. Ribozymes are specifically designed for a particular target, and the target message must contain a specific nucleotide sequence. They are also established expression modulators. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

A further mechanism for modulating expression on a post-transcriptional level, in particular to down-regulate gene expression is RNA interference (RNAi) which is a mechanism for RNA guided regulation of gene expression in which double-stranded ribonucleic acid molecules inhibit the expression of genes with complementary nucleotide sequences. Conserved in most eukaryotic organisms, the RNAi pathway is thought to have evolved as form of innate immunity against viruses and also plays a major role in regulating development and genome maintenance.

The RNAi pathway is initiated by the enzyme dicer, which cleaves double-stranded RNA (dsRNA) to short double-stranded fragments of usually approximately 20 to 25 basepairs. One of the two strands of each fragment, known as the guide strand, is then incorporated into the RNA induced silencing complex (RISC) and base-pairs with complementary sequences. The most well-studied outcome of this recognition event is a form of post-transcriptional gene silencing. This occurs when the guide strand basepairs with the messenger RNA (mRNA) molecule and induces degradation of the mRNA by argonaut, the catalytic component of the RISC complex. The short RNA fragments are known as small interfering RNA (siRNA) when they derive from exogenous sources and microRNA (miRNA) when they are produced from RNA coding genes in the cells' own genome.

The selective and robust effect of RNAi on gene expression makes it a valuable research tool, both in cell culture and in living organisms. Synthetic dsRNA introduced into cells can induce suppression of specific genes of interest. The effect of these genes on the phenotype of the cells can then be analyzed by studying the effect of the gene silencing. RNAi may also be used for large-scale screens that systematically shut down each gene in the cell, which can help identify the components necessary for a particular cellular process or an event such as for example, cell division.

Due to its advantages siRNA-mediated RNAi has become an indispensable tool in functional genomic research. Chemically synthesized siRNA reagents that target every gene in a human, mouse and rat genome are available for convenient delivery in vitro. Data acquired from RNAi experiments are used to support important conclusions about how genes function.

In addition to their role in the RNAi pathway, siRNAs also act in RNAi related pathways, for example as an antiviral mechanism or in shaping the chromatin structure of a genome; the complexity of these pathways is only now being elucidated.

For the above reasons, the RNA interference pathway is often exploited in experimental biology to study the function of genes in cell culture and in vivo in model organisms. Double-stranded RNA is synthesized with a sequence complementary to the target sequence of a gene of interest, usually a 18 to 30mer and introduced into the cell or organism, where it is recognized as exogenous genetic material and activates the RNAi pathway. Using this mechanism, researchers can cause a drastic decrease in the expression of the targeted gene. Studying the effects of this decrease can show the physiological role of the respective targeted gene product. Since RNAi may not necessarily totally abolish expression of the gene, this technique is sometimes referred to as a "knockdown" to distinguish it from "knockout" procedures in which expression of a gene is entirely eliminated, e.g. by introducing a knock-out mutation in the target gene.

Depending on the organism and the experimental system, the exogenous RNA may be a long strand designed to be cleaved by dicer or short RNAs designed to serve as siRNA substrates. In most mammalian cells, shorter RNAs are used because long double-stranded RNA molecules induce the mammalian interferon response, a form of innate immunity that reacts non-specifically to foreign genetic material.

These molecules are usually introduced in the cells by appropriate transfection methods.

Specialized laboratory techniques have also been developed to improve the utility of RNAi in mammalian systems by avoiding the direct introduction of siRNA, for example, by stable transfection with a plasmid encoding the appropriate sequence from which siRNA can be transcribed, or by more elaborate lentiviral vector systems allowing the inducible activation or deactivation of transcription, known as conditional RNAi.

In order to ensure that the conclusion drawn from any expression modulating experiment such as e.g. an antisense or a RNAi experiment are accurate, it is important to include proper controls in every expression modulating experiment. Such controls strengthen the drawn conclusions and ensure that the performed expression modulating experiments result in the expected silencing. Appropriate experimental controls are thus of utmost importance in order to maximize the value of the generated data.

Commonly, at least three types of control samples are run e.g. in every RNAi experiment: a positive control, a negative control and an untreated control. Positive controls may monitor efficiency of e.g. siRNA delivery into cells (transfection efficiency) and negative controls distinguish sequence-specific silencing from non-specific effects. Untreated samples determine the baseline level of cell viability, the cell phenotype and the target gene level. There are also assay specific positive controls to validate that a detection assay is working properly.

In order to achieve successful gene silencing, efficient delivery of the expression modulating compound such as a siRNA into the cells of interest is important. E.g. siRNA delivery efficiency can vary between individual cell types used and the delivery method used.

In RNAi experiments, as positive controls usually siRNA are used that target a housekeeping gene. Popular target genes are for example GAPDH, lamin, MAPK1, BetaActin, p53, cyclophilin B and luciferase. The positive controls as are presently often aimed at in the state of the art target a housekeeping gene that this constitutively and abundantly expressed in a wide variety of cell types. Many positive controls demand elaborate and time-consuming testing methods. Many researchers are currently using quantitative RT-PCR or western blotting to assess the compound induced knockdowns. While accurate, these techniques can be very time-consuming and labor intensive. Another means to monitor expression modulating compound/siRNA delivery is the use of fluorescently labeled compounds/siRNAs. This method has the advantage of speed, but it can be unreliable since the compounds/siRNA can be trapped in endosomes or other subcellular compartments that keep the expression modulating compound such as a siRNA from targeting their target mRNA.

Functionally validated siRNAs can also be used as positive controls. Gene silencing mediated by them is usually determined either on the mRNA or on the protein level. These analyses, however, are very elaborate and time-consuming. This has the effect that at the time, when one wants to interpret e.g. HTS experiments, one does not have the information regarding the gene silencing effect obtained with the positive controls. Therefore, one has to perform part of the experiments and interpretation without the information regarding their comparability. This has the effect that sometimes one must discard portions of the already obtained primary data (for example when the transfection did not function efficiently).

Furthermore, gene silencing effects which are caused by siRNA transfection in eukaryotic cells have a transient character. If one wants to perform RNAi experiments with siR-NAs in a high-through put screening assay (HTS) one must prepare the whole series of experiments on a plurality of e.g. microtiter plates in multiple replicas. Due to many factors which influence the transfection efficiency of the used cellular systems (for example the kind of cells, charge fluctuations of the used transfection reagents and the like) it is not always easy to compare experiments, that were done on different days or to compare gene silencing effects which were done with different culture plates. For this purpose, a validated positive control siRNA, which is run on each individual plate and in each experiment, would be helpful that can be used in order to normalize the measured gene silencing effect. As most HTS experiments are interpreted by phenotypic analysis methods, a positive control, wherein the successful transfection leads to a clear, easy to identify phenotype, would be a valuable tool for the respective user.

A phenotype which is rather easy to determine via microscopic techniques is apoptosis and thus cell death. In particular in the case of adherent cells, dying (apoptotic or necrotic) cells changes their morphology in a very characteristic way, as they round up and detach from the surface they adhered to. Therefore, the silencing of genes with siRNAs which induce apoptosis in the cell is a promising possibility to develop a phenotypic control siRNAs.

Therefore, toxic siRNAs are used as positive controls. The intent is that when this siRNA is employed, and a transfection in gene silencing is properly executed, this control will kill the cells which are successfully transfected. Thus, a visual check is all that is needed to confirm that transfection is working probably.

For example Dharmacon has developed a toxic siRNA, which may induce cell death as a phenotypic detectable effect. However, scientific publications show that this siRNA does not induce a detectable cell death e.g. in HEK 293 cells (Reynolds et al, 2006). Further experiments also showed that this toxic siRNA can also not induce cell death in A 549, Hoh7 and HepG2 cells. The applicability is thus limited.

Furthermore, toxic controls usually target a critical gene, which when successfully targeted results in loss of a critical protein in death of the cell. However, this approach is problematic. It is surprisingly difficult to target a single gene and ensure cell death. Cell type, metabolic state, whether the target is expressed and many other variables make the efficacy of such a single-gene toxic control difficult to predict.

There is thus a strong need for a siRNA or a siRNA composition, which induces phenotypically detectable apoptosis in many cell lines and primary cell preparations which can thus be used as a reliable phenotypic control.

It is the object of the present invention to provide a positive control for use an expression modulating experiments, in particular RNAi experiments which is effective and convenient to analyze.

This object is solved by using an apoptosis inducing gene expression modulating compound targeting a repetitive element present in an untranslated region, preferably the 3' UTR of protein coding gene transcripts as a positive control in a gene expression modulating assay, such as an RNAi experiment.

The invention is based on the fact that there are repetitive elements that are repeated (often hundreds to thousands of times) in the genome. These elements are often species specific and are also present in untranslated regions, in particular many 3' UTRs (three prime untranslated regions) of protein coding gene transcripts. The apoptosis inducing expression modulating compound of the present invention which is preferably an RNAi compound such as a siRNA, deliberately targets a conserved repetitive element that occurs in many genes. This repetitive element may occur in more than 100, 200, 500, 800 or even more than 1000 genes. By targeting and thereby silencing several to hundreds of gene transcripts (comprising the targeted repetitive element in an untranslated region, in particular the 3'UTR) the apoptosis inducing compound severely disturbs the function of the cell thereby basically acting as a broad-spectrum toxic expression modulating compound effectively inducing apoptosis and thus killing the cells. By using this multiple target approach the invention departs from conventional approaches which aim at silencing specific genes. The prior art designed the siRNAs as specific as possible for a certain target gene in order to specifically induce silencing of the specific target gene and to avoid off-target effects on other transcripts. The invention uses a different approach by designing an expression modulating compound such as a siRNA to target as many genes as possible by targeting a repetitive element in an untranslated region, preferably the 3' UTR of a transcript thereby disturbing the cell function and efficiently inducing apoptosis.

Apoptosis leads to phenotypic changes in the cells, which can for example be detected by using a microscope by assessing gross changes in cellular morphology and number. Also commercially available 'live-dead' colorimetric or fluorogenic or luminescence based assays can be used in order to detect/determine apoptosis which are assessed by microscopic imaging or by plate based imaging technologies. Thereby, an efficient positive control is provided for use in an expression modulating assay, which is easy to determine based on the phenotype of the presented cells or by a simple colorimetric based assay. Thereby, an easy and quickly to analyse positive control is provided. Due to the fact that the invention uses a universal targeting approach the positive control according to the present invention also works in numerous different cells. Basically, the positive control according to the present invention will work in all cells, which comprise the repetitive element the expression modulating compound targets in the transcript.

Furthermore, also the species specificity of the positive control can be controlled by choice of the repetitive element that is targeted. The apoptosis inducing expression modulating compound can be species-specific or may show cross-species specificity. The use of expression modulating compounds showing a cross-species specificity and which accordingly silence e.g. the expression of the corresponding genes in e.g. rat, mouse and/or human cells has the advantage that the positive control can be used for a variety of cells. However, the expression modulating compound may also be specific for at least one cell species, selected from the group consisting of primate cells such as human cells, rodent cells such as rat cells and mouse cells. For example, by choosing a repetitive element that is for example specific for a human cell, for example, the Alu repeat, a positive control is created, which is specific for human cells. An equivalent approach can be taken for example for providing a mouse specific siRNA positive control targeting a mouse specific repetitive element, for example, the B1 repeat. A corresponding approach can also be used for any other kind of species. Accordingly, if one wants to design an expression modulating compound such as an siRNA compound that efficiently works as a positive control in different cell species (for example human, mouse and rat cells) one would chose a repetitive element which is present in the genome of all the respective species. Furthermore, if one wants to design an expression modulating compound such as an siRNA compound that efficiently works as a positive control in a specific cell species (for example human or primate cells) one would chose a repetitive element which is present in the genome of said respective species.

As apoptosis is induced very efficiently by the positive control of the present invention, it is also detectable within a rather short time frame. As is shown in the experimental section, the apoptosis is detectable already as early as 72 or even 48 hours or less after transfection when using the positive control according to the present invention. Because regular laboratory equipment such as a microscope can be used for analyzing the positive control, the analysis of the positive control according to the present invention can be performed very easily using established systems.

As defined above, the repetitive element targeted by the expression modulating compound can be species specific, e.g. specific for human cells. Using the approach of the present invention, apoptosis was induced in several different human cell lines, such as HeLa S3, Huh 7, 293 and HepG2 cells, when the Alu repetitive element was targeted and in rodent cells, in particular mouse and rat cells, when the B1 repetitive element was targeted.

Many compounds may be used in order to regulate the expression on a post-transcriptional level. Examples of appropriate expression modulators include but are not limited to small organic molecules, nucleic acids, peptides, cyclic peptides, antisense molecules, RNAi molecules, and ribozymes. Respective modulators are well-known to the skilled person and were also outlined above. Please refer to our above comments for details.

According to one embodiment, the expression modulating compound is an RNAi modulating, i.e. an RNAi inducing respectively mediating compound. Examples of RNAi mediating compounds include but are not limited to short interfering nucleic acids (siNA), short interfering RNA (siRNA), microRNA (miRNA) and short hairpin RNAs (shRNA) as well as precursors thereof which are processed in the cell to the actual RNAi mediating compound. Preferably, said compound is a siRNA. As siRNA, said compound is a double-stranded molecule preferably having 3' overhangs on each strand. Said siRNA compound may comprise desoxy—as well as ribonucleotides and furthermore, modified nucleotides. Several embodiments and variations of siRNA compounds are known and can be used in conjunction with the present invention. The length of said siRNA is usually between 18 and 35 nt, preferably between 19 and 27 nt. The 3' overhangs on each end if present are preferably 2 nts long, but blunt ended molecules may also be used. In order to efficiently induce silencing, the siRNA used as RNAi modulating compound is substantially complementary to a portion of the target gene transcript for inhibiting the expression of said target transcript by RNA interference. Suitable siRNAs targeting the chosen/identified target sequences of the target genes on the RNA level can be identified by using proper computational methods, applying certain design-algorithms. Several methods are known and can be used in conjunction with the present invention in order to provide suitable siRNAs.

In order to obtain a siRNA of the above structure against the target transcript, the double-stranded molecule can be transfected directly into the cell. Alternatively, this structure may result by processing by dicer, an enzyme that converts either long dsRNAs or small hairpin RNAs (shRNAs) into siRNAs (see above). These precursors or the final siRNA molecules can be produced exogenously (artificially) and can then be introduced into the cells to be analyzed by various transfection methods, to analyze the specific knockdown of the target genes involved in apoptosis.

According to one embodiment, the expression modulating and in particular the RNAi modulating compound is expressed by a vector. This embodiment is advantageous, as e.g. transfection of an exogenous siRNA or antisense molecule can be sometimes problematic, since the gene knockdown effect is only transient, particularly in rapidly dividing cells. One way of overcoming this challenge is to modify the expression modulating compound such as a siRNA in such a way as to allow it to be expressed by an appropriate vector, for example a plasmid. For siRNA, this is done by the introduction of a loop between the two strands, thus producing a single transcript, which can be then processed into a functional siRNA in the cell. Such transcription cassettes typically use an RNA polymerase 3 promoter (for example U6 or H1) which usually direct the transcription of small nuclear RNAs (shRNAs) (U6 is involved in gene's placing; H1 is the RNA subcomponent of human RNAse p). It is assumed that the resulting shRNA transcript from the vector is then processed by dicer, thereby producing the double-stranded siRNA molecules, preferably having the characteristic 3' overhangs.

According to one embodiment, the targeted repetitive element sequence has at least one of the following characteristics:

(a) A length suitable for efficient targeting by RNAi. Typically >50 bases is sufficient, but sequences as small as 21 bases could also work, depending on the repetitive element and its sequence.
(b) It is an interspersed repetitive element. Interspersed repetitive DNA is found in all eukaryotic genomes.

Typical representatives of suitable repetitive elements are SINES (short interspersed nuclear element) and LINES (long interspersed nuclear element). Examples are Alu in primates and B1 in rodents. Alu sequences are about 300 base pairs long and are therefore classified as short interspersed nuclear elements (SINES) amongst the class of repetitive DNA elements. Alu elements usually do not contain coding sequences, and can be recognized by the restriction enzyme AluI. There are over one million Alu sequences interspersed throughout the human genome, and it is estimated that about 10% of the mass of the human genome consists of Alu sequences. Alu sequences are retrotransposons and look like DNA copies made from RNA polymerase III-encoded RNAs. Most human Alu sequence insertions can be found in the corresponding positions in the genomes of other primates, but about 7,000 Alu insertions are unique to humans. The short interspersed nuclear (SINE) Alu elements in humans and the analogous B1 and B2 elements in rodents, in particular mice have succeeded in becoming the most abundant mobile elements within the genomes. Usually, Alu-sequences are often duplicated internally, which means that they comprise a 5' section and a 3' section which are related to each other, usually they are homologous. Usually, the Alu sequences are flanked by two short sequences (usually 7 to 20 bp), so-called direct repeats.

There are SINES and LINES known for other species as well, e.g for pig which could also be used according to the principles of the present invention. Sequences of SINES and LINES are available in the NCBI and EMBL public databases. Anyone skilled in the art can find a species specific sequence and e.g. apply known siRNA design rules to develop a species specific, cell type non specific toxic control or a respective control showing a cross-specificity (see above). As is outlined above, also other expression modulating compounds such as other RNAi mediating compounds or antisense molecules can be used.

(c) It comprises a sequence conserved enough to select a target sequence, preferably a 21mers that are of sufficient complementarity to function (there are 23000 entries in Genbank that contain Alu repeats), and in particular to mediate RNAi effects.

According to a preferred embodiment, the target sequence is selected from the group consisting of:

```
1727   CCTCCCAAAGTGCTGGGATTA   (SEQ. ID No. 1)

1572   CACCTGTAATCCCAGCACTTT   (SEQ. ID No. 2)

1336   CTGGAGGCTGAGGCAGGAGAA   (SEQ. ID No. 3)

1278   AAGCCTGTAATCCCAGCACTT   (SEQ. ID No. 4)
```

According to the standard applied in the prior art, the target sequence is indicated/shown as the corresponding DNA sequence. The expression modulating compound, and in particular the RNAi mediating compound can be designed based upon said sequence using conventional methods to recognize said target sequence and to efficiently induce silencing, preferably via RNAi. As is outlined above, in case the RNAi mediating compound is a siRNA compound, it may comprise ribose—as well as desoxyribose nucleotides or modified nucleotides.

In particular, siRNAs designed based upon the target sequences of Seq. ID. No 2 and 4 efficiently induced apoptosis when introduced in the cells.

As can be seen, sequences Seq. ID. No 2 and 4 are rather similar and share a common consensus. siRNAs respectively designed based upon said sequence target the same well conserved region of the human Alu repetitive element:

```
CCTGTAATCCCAGCACTT.      (SEQ. ID No. 5)
``` siRNAs or other expression modulating compounds which can be used for knocking down the expression of several genes are designed based upon the chosen target sequence using standard methods. Therefore, the present invention also provides the corresponding siRNAs as well as other expression modulating compounds, in particular RNAi compounds which can be advantageously used as positive controls in RNAi experiments.

The Alu family has polymorphisms—there are numerous nucleotide differences between family members. The attempt was to pick well conserved sequences and then screen for physiological effect. The siRNAs designed based upon the chosen target sequences targets a subset of Alu.

According to a further embodiment, the apoptosis inducing expression modulating compound targets a B1 repetitive element. The target sequence of a B1 repetitive element may be selected from the group consisting of

```
B1_1:   CAGGCGGATTTCTGAGTTCGA   (SEQ. ID No. 6)

B1_2:   AGCCAGGGCTACACAGAGAAA   (SEQ. ID No. 7)

B1_3:   CAGAGGCAGGCGGATTTCTGA   (SEQ. ID No. 8)

B1_4:   CATGGTGGCGCACGCCTTTAA   (SEQ. ID No. 9)
```

A correspondingly designed RNAi mediating compound against such B1 repetitive elements and in particular a siRNA targeting the respective B1 repetitive element is specific for mouse and rat cells. As is shown in the examples, a siRNA against a respective target sequence is very effective in inducing apoptosis in mouse and rat cells. Furthermore, also expression modulating compounds targeting different combinations of the above mentioned target sequences can be used in conjunction with the present invention.

According to a further embodiment, a combination of an expression modulating compound targeting a repetitive element as described above and an expression modulating compound targeting the expression of a gene involved in a central metabolic process of the cell is used as a positive control in an expression modulating assay. This has the particular advantage that the effectivity of the positive control can be enhanced, e.g. by reducing the time necessary for achieving a visible apoptotic phenotype.

A gene involved in a central metabolic process is in particular a gene that is relevant for the proper maintenance of the cell viability and thus e.g. a gene involved in the cell cycle, apoptosis, cell division, DNA transcription, replication and repair or cell differentiation and development. Silencing of a respective gene induces, respectively promotes apoptosis. A suitable example for a respective gene is the ubiquitin gene.

Ubiquitin is a small protein that occurs in all eukaryotic cells. It performs a myriad of functions through conjugation to a large range of target proteins. A variety of different modifications can occur. The ubiquitin protein is highly conserved among eukaryotic species. A protein is marked with ubiquitin (ubiquitylation or ubiquitination) by a series of steps. Following addition of a single ubiquitin moiety to a protein substrate (monoubiquitination), further ubiquitin molecules can be added to the first, yielding a polyubiquitin chain. The ubiquitination system functions in a wide variety of central cellular processes, including apoptosis, cell cycle and division, DNA transcription and repair and differentiation and development.

The target sequence for ubiquitin may be selected from the group consisting of

```
Ubb_cs1    AAGGCCAAGATCCAGGATAAA    (SEQ. ID No. 10)

Ubb_cs2    AAGTTTAGAAATTACAAGTTT    (SEQ. ID No. 11)

Ubb_cs3    CGGCAAGACCATCACCCTGGA    (SEQ. ID No. 12)

Ubb_cs4    CGTGAAGACCCTGACCGGCAA    (SEQ. ID No. 13)
```

A correspondingly designed RNAi mediating compound against ubiquitin B and in particular a siRNA targeting the respective ubiquitin B target sequence silences the expression of ubiquitin B in human, mouse and rat cells as it matches the human, mouse and rat gene.

Furthermore, the target sequence may be selected from the group consisting of

```
Ubb_hs1:   CCTGTTCAAAATGTTAATAAA   (SEQ. ID No. 14)

Ubb_hs2:   AAGGCCAAGATCCAAGATAAA   (SEQ. ID No. 15)

Ubb_hs3:   CAGGATCCTGGTATCCGCTAA   (SEQ. ID No. 16)

Ubb_hs4:   CCAACTTAAGTTTAGAAATTA   (SEQ. ID No. 17)
```

A correspondingly designed RNAi mediating compound against human ubiquitin and in particular a siRNA targeting the respective human ubiquitin target sequence silences the expression of ubiquitin B in human cells. Thus, correspondingly designed RNAi mediating compounds show a specificity for human cells.

According to a one embodiment, a combination of
a) a RNAi inducing compound targeting the transcript of a ubiquitin gene, preferably ubiquitin B and
b) a RNAi inducing compound targeting the transcript of at least one SINE element, preferably an Alu or B1 repetitive element;
is used as positive control in an RNAi assay.

Therefore, a combination of an expression modulating compound targeting a repetitive element, in particular a SINE element such as an Alu or B1 repetitive element in the untranslated region of a transcript and an expression modulating compound targeting the expression of ubiquitin may be used as a positive control in an expression modulating assay. As is shown in the examples, the respective combination effectively induces apoptosis in a large variety of cells. According to one embodiment, the following target sequences are targeted by the combination of expression modulating compounds:

```
Cs_ubb_4:  CGTGAAGACCCTGACCGGCAA    (SEQ. ID No. 13)
           (ubiquitin b)

B1_4:      CATGGTGGCGCACGCCTTTAA    (SEQ. ID No. 9)
           (B1 repetitive element)
```

As is outlined above, Cs_ubb_4 matches to mouse, rat and human ubiquitin B. The siRNA targeting the respective B1 repetitive elements is specific for mouse and rat cells. As is shown in the examples, a combination of siRNAs against the respective target sequences is very effective in inducing apoptosis. Furthermore, also expression modulating compounds targeting different combinations of the above mentioned target sequences can be used in conjunction with the present invention.

A further example for a gene involved in a central metabolic pathway is the Plk1 gene (polokinase 1). Plk1 is an enzyme that catalyzes the chemical reaction of ATP and a protein to ADP+a phosphoprotein. Thus, the two substrates of this enzyme are ATP and a protein, whereas its two products are ADP and phosphoprotein. This enzyme belongs to the family of transferases, specifically those transferring a phosphate group to the sidechain oxygen atom of serine or threonine residues in proteins (protein-serine/threonine kinases). This enzyme participates in particular in several metabolic pathways, thereunder the cell cycle.

According to a further embodiment, a combination of
a) a RNAi inducing compound targeting the transcript of the plk1 gene, and
b) a RNAi inducing compound targeting the transcript of at least one SINE element, preferably an Alu or B1 repetitive element;
is used as positive control in an RNAi assay.

The target sequence for plk1 may be selected from the group consisting of

```
cs_plk1-857:   CAGTATTCCCAAGCACATCAA (SEQ. ID No. 18)

cs_plk1-1604:  CCGCAGCGCCATCATCCTGCA (SEQ. ID No. 19)

cs_plk1-174:   CCGGAGGTCCTAGTGGACCCA (SEQ. ID No. 20)

cs_plk1-1403:  CCTGCAGTACATAGAGCGTGA (SEQ. ID No. 21)
```

A correspondingly designed RNAi mediating compound against plk1 and in particular a siRNA targeting the respective plk1 target sequence silences the expression of plk1 in human, mouse and rat cells as it matches the human, mouse and rat gene.

Furthermore, the target sequence for plk1 may be selected from the group consisting of

```
plk1-2083:   CACCATATGAATTGTACAGAA (SEQ. ID No. 22)
plk1-935:    AACCATTAACGAGCTGCTTAA (SEQ. ID No. 23)
plk1-2151:   TAAACAGATGTGAATATTCAA (SEQ. ID No. 24)
plk1-1473:   AAGAAGATCACCCTCCTTAAA (SEQ. ID No. 25)
plk1-542:    CTGCCAGTACCTGCACCGAAA (SEQ. ID No. 26)
plk1-2146:   CACATTAAACAGATGTGAATA (SEQ. ID No. 27)
plk1-278:    CAAGGAGGTGTTCGCGGGCAA (SEQ. ID No. 28)
plk1-1631:   CAACGGCAGCGTGCAGATCAA (SEQ. ID No. 29)
plk1-1637:   CAGCGTGCAGATCAACTTCTT (SEQ. ID No. 30)
```

A correspondingly designed RNAi mediating compound against the human plk1 gene, and in particular a siRNA targeting the respective plk1 target sequence, silences the expression of plk1 in human cells.

Appropriate RNAi mediating compounds such as siRNAs which bind the corresponding mRNA transcript can be designed based upon said target sequence according to methods which are well-known and also well established. Targeting of the corresponding transcripts by the RNAi inducing compounds results in efficient gene silencing.

In case a combination of expression modulating compounds is used, said expression modulating compounds can be transfected into the cells either at the same time, for example by using a transfection composition comprising both (in case two expression modulating compounds are used) expression modulating compounds or by sequentially introducing the expression modulating compounds into the cells. It is also within the scope of the present invention to use further expression modulating compounds which silence further target genes involved in apoptosis or leading to apoptosis.

The degree of apoptosis induced by the expression modulating compound or combination of expression modulating compounds according to the present invention is preferably between 10% to 100%, 25% to 100%, 50% to 100% or 75% to 100%. There is also a utility of toxic sequences that are not extremely toxic as they may serve as better indicators of delivery efficiency, as one needs an optimized delivery to see their effect.

According to one embodiment, the expression modulating compounds and/or the respective combination can be efficiently used for transfection in a concentration selected from the group consisting of at least 5 nM, at least 10 nM, at least 25 nM and at least 50 nM.

Furthermore, a method for performing an expression modulating analysis or assay is provided, wherein an apoptosis inducing expression modulating compound targeting a repetitive element present in the untranslated region, in particular the 3' UTR of protein coding gene transcripts is introduced into cells to induce apoptosis in said cells and is used as a positive control.

As outlined above, using an expression modulating compound targeting a repetitive element present in the untranslated region, in particular the 3' UTRs of protein coding gene transcripts has the advantageous effect that several different genes are silenced by said compound thereby disturbing the cell metabolism and inducing apoptosis leading to a visually detectable phenotype.

Further embodiments/features of this method and characteristics of the expression modulating compound as well as suitable target sequences were already outlined above in conjunction with the description of the use of respective expression modulating compounds as positive controls. These features/embodiments equally apply to the provided method according to the present invention. This in particular pertains to the defined examples of expression modulating compounds and combinations of expression modulating compounds and the embodiment, wherein the effect of said expression modulating compound such as an RNAi modulating compound on the expression of the target genes involved in apoptosis is analyzed by microscopy technologies.

As is also outlined above, the RNAi modulating/mediating compound can be a siRNA. The siRNA is preferably substantially complementary to a portion of the respective target gene transcript for inhibiting the expression of said target transcript by RNA interference. Suitable examples of target sequences, respective siRNAs and ways to generate them are described above and are known in the prior art and equally apply to the provided method.

Also provided is an expression modulation analysis kit, in particular for performing RNAi experiments, comprising an apoptosis inducing expression modulating compound targeting a repetitive element present in the untranslated region, in particular of 3' UTRs of protein coding gene transcripts as a positive control.

As outlined above, silencing is preferably achieved via RNAi. Further details of the positive control, combinations and preferred embodiments are outlined above and also apply to the kit. We refer to the above disclosure.

The kit may also comprise further components, such as other expression modulating compounds such as e.g. siRNAs for knockdown of the desired target genes, negative controls, reagents, such as for example transfection reagents and/or buffers.

A respective kit allows the rapid detection of the transfection efficiency by using the positive controls according to the present invention which forms an essential part of said kit. As is outlined above, the phenotype induced by the compound according to the present invention leads to an apoptotic phenotype that can be detected in less than 72 hours. Preferably, said phenotype is detectable in less than 60 hours and even less than 50 hours.

As is outlined above, phenotypic controls are particularly suitable for high through put assays, wherein several experiments are performed in parallel using a substrate comprising several reaction spots, such as for example a microtiter plate (having multiple wells) or a transfection chip (comprising multiple hydrophilic spots surrounded by hydrophobic areas). The expression modulating compounds that are used for the HTS experiments are often ordered by the customer in a ready to use form and the manufacturer then provides the compounds, e.g. siRNAs, already in the reaction spots of the substrate in the desired arrangement. Hence, the positive control according to the present invention can be provided in a reaction spot of the substrate, such as for example in a well of a microtiter plate or on a hydrophilic spot of a transfection chip. The other reaction spots may comprise the experimental expression modulating compounds, such as siRNAs. The customer then only needs to add the cells and proper media for cell growth and start the analysis.

Therefore, the invention also provides a substrate comprising multiple reaction spots suitable for performing tansfection reactions (for example a microtiter plate comprising wells or a wall-less setting on a transfection chip comprising multiple hydrophilic reaction spots surrounded by hydrophobic areas), wherein at least one of said reaction spots comprises an apoptosis inducing expression modulating compound targeting a repetitive element present in an untranslated region, preferably the 3' UTR of protein coding gene transcripts as a positive control.

Therefore, the positive control according to the present invention is already provided in/on the substrate and can therefore be easily incorporated in the experiments. Optionally, the substrate may also comprise further expression modulating compounds used in the actual experiments, such as for example customized RNAi compounds, such as siRNAs.

Further details regarding said positive control are described in detail above; we refer to the above disclosure.

The present invention is now described by way of non-limiting examples.

EXAMPLES

Example 1

21 base sequences were randomly screened for frequency of appearance in the NCBI-refseq database. A number of sequences were identified that appeared more than one thousand times in mRNAs and had reasonably high biopred scores (indicators of suitability as bioactive siRNAs). Four of theses sequences, which appeared between 1,200 and 1,700 times in the refseq database (unique human mRNA collection) were chosen for a functional analysis. Many of the sequences corresponded to the human Alu repetitive element. These were the following sequences which were also chosen for testing:

```
1727   CCTCCCAAAGTGCTGGGATTA   (SEQ. ID No. 1)
1572   CACCTGTAATCCCAGCACTTT   (SEQ. ID No. 2)
1336   CTGGAGGCTGAGGCAGGAGAA   (SEQ. ID No. 3)
1278   AAGCCTGTAATCCCAGCACTT   (SEQ. ID No. 4)
``` siRNAs were produced based upon the selected target sequence and were transfected into mammalian cells and the cells were examined 24 to 48 hours after transfection. Three of the siRNAs showed a profound effect on the survival of the cells. Apparently, all four of the siRNA sequences identified mapped to a single repetitive element, disseminated throughout the transcriptome. As the Alu repeat is primate specific, it is not conserved in the refseq mouse and rat NCBI databases. Therefore, the siRNAs described above were all targeting a species specific highly repetitive element in the 3'UTR of human protein coding transcripts. The non-conversation of the repetitive sequence in mouse and rat also opens up the possibility of using these siRNAs as species specific toxic controls. They can be used e.g. as delivery controls in xenographic tumor models, in which human tumor cells are grown in animal models. The toxic expression modulating compounds of the present invention would only target the implanted human cells but would not affect the mice cells/tissue. This provides a novel, valuable delivery control for gene silencing experiments in xenograph animal models of human disease.

Figure 1:
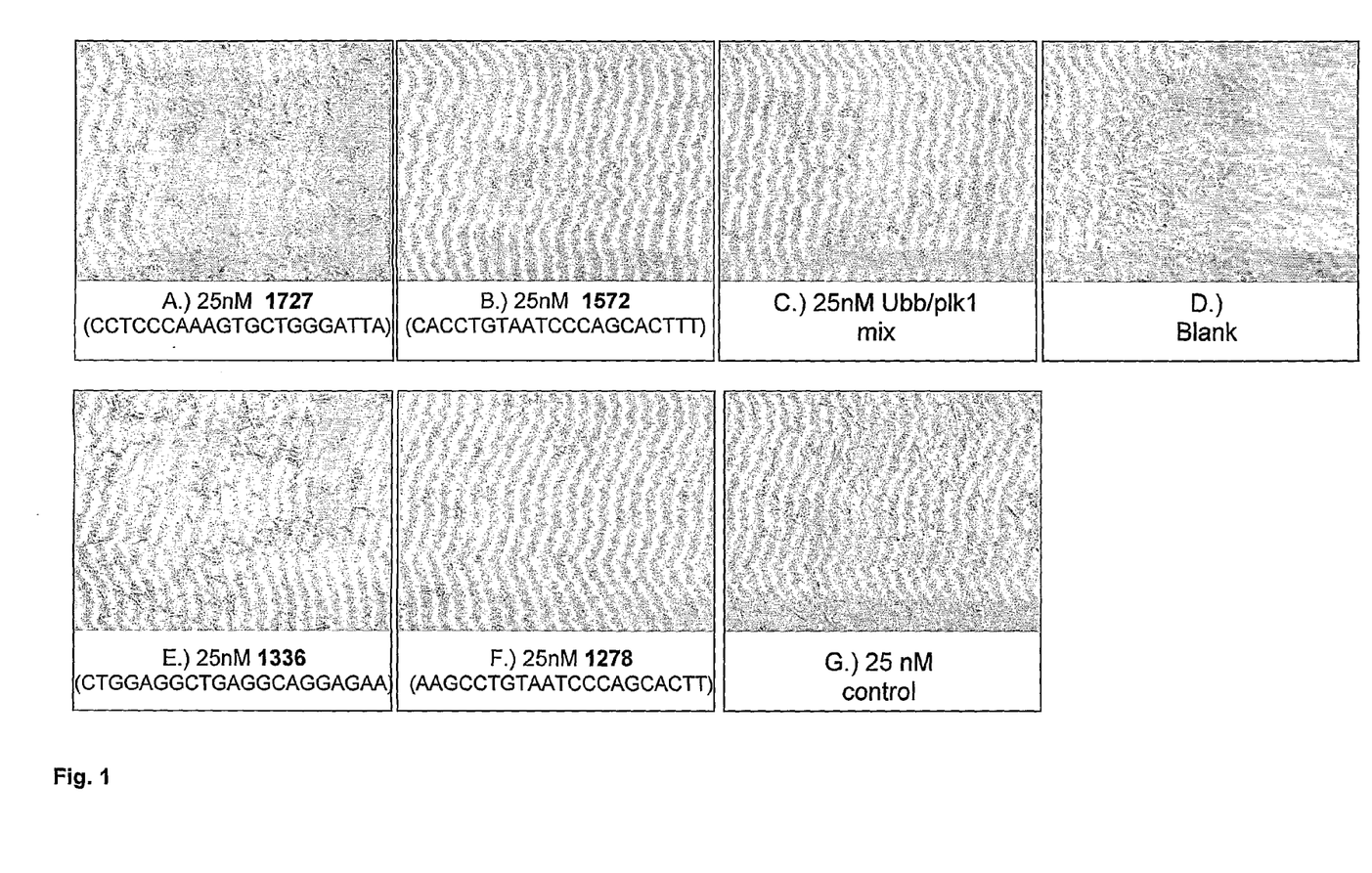
FIG. 1 shows the results of transfection experiments performed in Example 1.

The results of the performed transfection experiments are shown in FIG. 1.

25 nM of the siRNAs were transfected into the cells, which were HeLa S3 cells. The analysis was performed 27 hours after the transfection. FIGS. 1a, b, e and f show the results that were obtained with the siRNAs according to the present invention, which target highly repetitive elements in the 3'UTR of protein coding transcripts, thereby silencing the corresponding genes. 25 nM were transfected in each cell. As can be seen, the sequences used in FIGS. 1b and 1f induced very efficiently apoptosis. Only a few cells are left which have a very round shape and thus show an apoptotic phenotype. The results are comparable to the ones obtained with FIG. 1c, wherein a mixture of two siRNAs targeting the ubiquitin and the Plk1 gene were transfected. The present invention thus provides a good alternative to other technologies, with a broader spectrum of applicability to more varied cell types. The sequences 1727 (SEQ. ID No. 1) and 1337 (SEQ. ID No. 3) would be useful to obtain an intermediate phenotype. Respectively designed siRNAs were less effective but still had broad cell type coverage.

FIG. 1d shows a blank experiment, wherein no substance was added. The blank thus shows the phenotype of untreated cells. FIG. 1g shows a control, wherein 25 nm of the OIAGEN Allstar negative control was used, a control that does not target any gene in humans.

Example 2

Fast forward transfection assays with siRNAs targeting the expression of ubiquitin B and B1 repetitive elements were performed:

```
Cs_ubb_4:   CGTGAAGACCCTGACCGGCAA    (SEQ. ID No. 13)
            (ubiquitin b)

B1_4:       CATGGTGGCGCACGCCTTTAA    (SEQ. ID No. 9)
            (B1 repetitive element)
```

Figure 2:
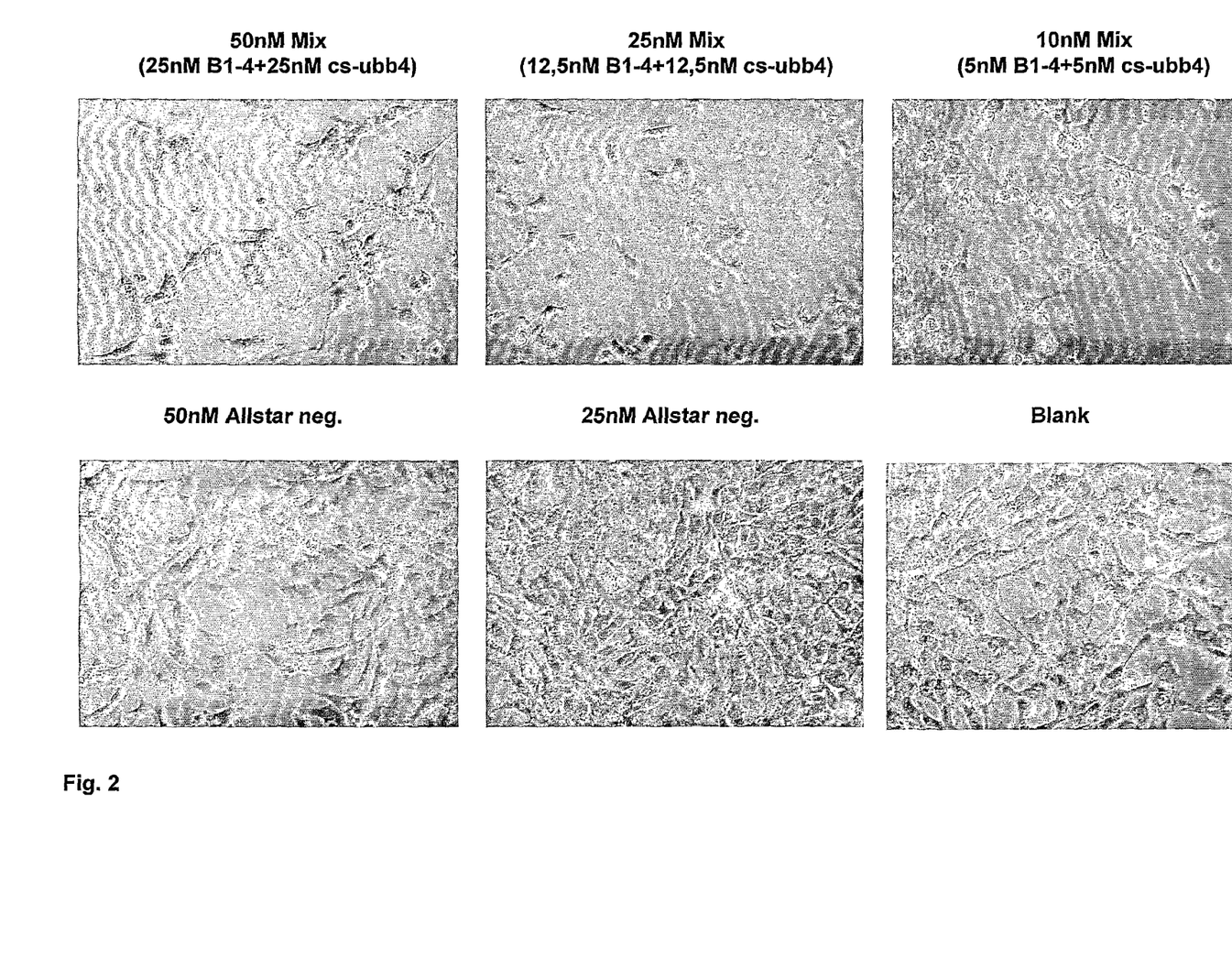
FIG. 2 shows the results of transfection experiments performed in Example 2.

$2 \times 10^4$ cells were used per well. 50, 25 or 10 nM siRNA were mixed with 3 ul (microliter) of a transfection reagent, here a cationic lipid transfection agent. The transfection complexes were used with 100 ul and 500 ul cell suspension. The results show that the mixture of expression modulating compounds, here siRNAs, targeting the cross-species specific ubiquitin (ubb4) and B1 repetitive sequence (B1-4) works very efficiently at 10 nM. In FIG. 2, NIH3T3 cells were used. FIG. 2 shows the results obtained 48 h after transfection.

Example 3

Figure 3:
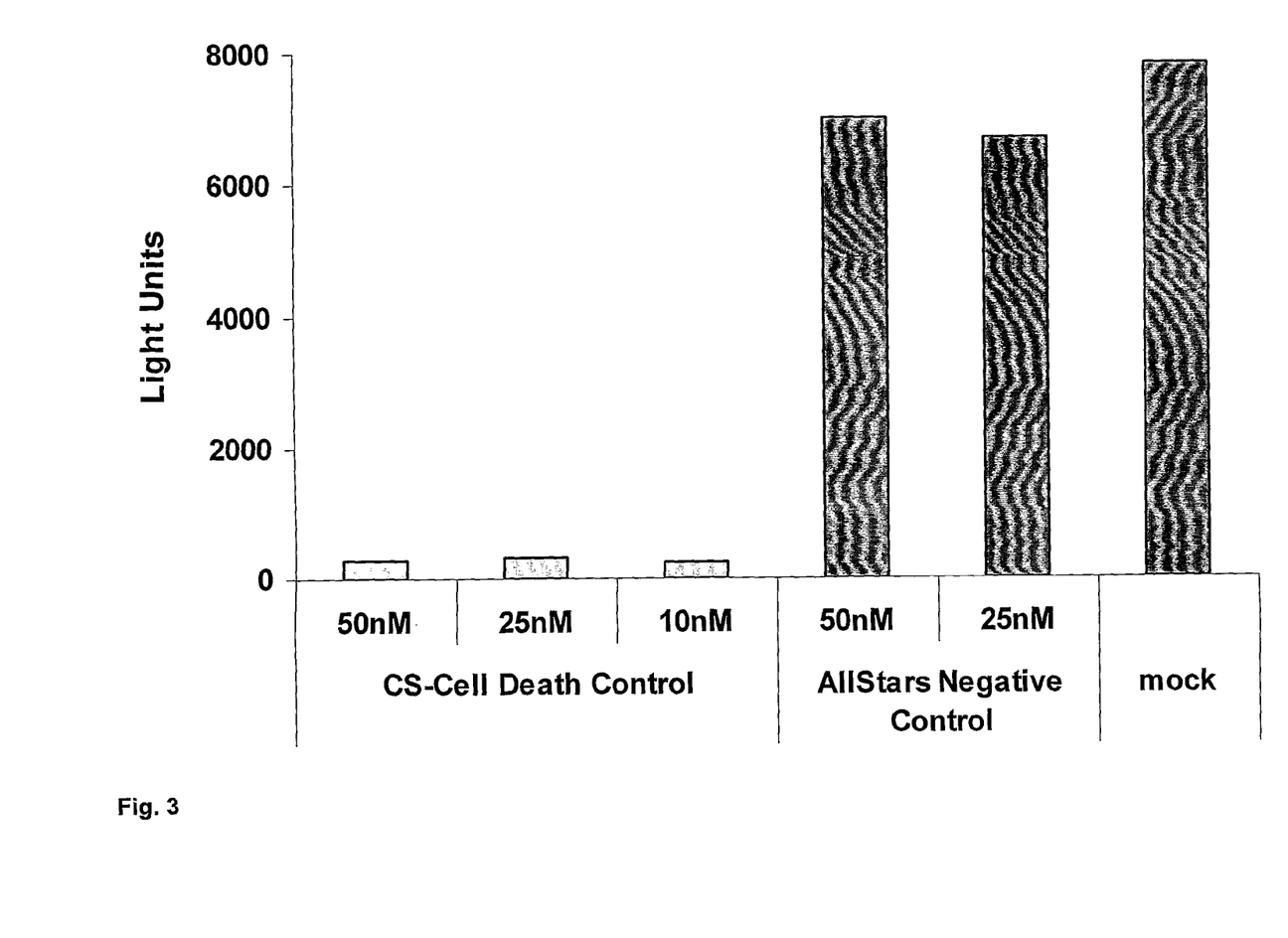
FIG. 3 shows the results of a quantification of cell numbers as described in Example 3.

FIG. 3 shows the results of a quantification of cell numbers using CellTiter Glo Assay (Promega) (mock=blank). The results show significant induction of cell death upon transfection with the siRNA mixture that was also used in example 2 (CS-cell death control).

Example 4

Figure 4:
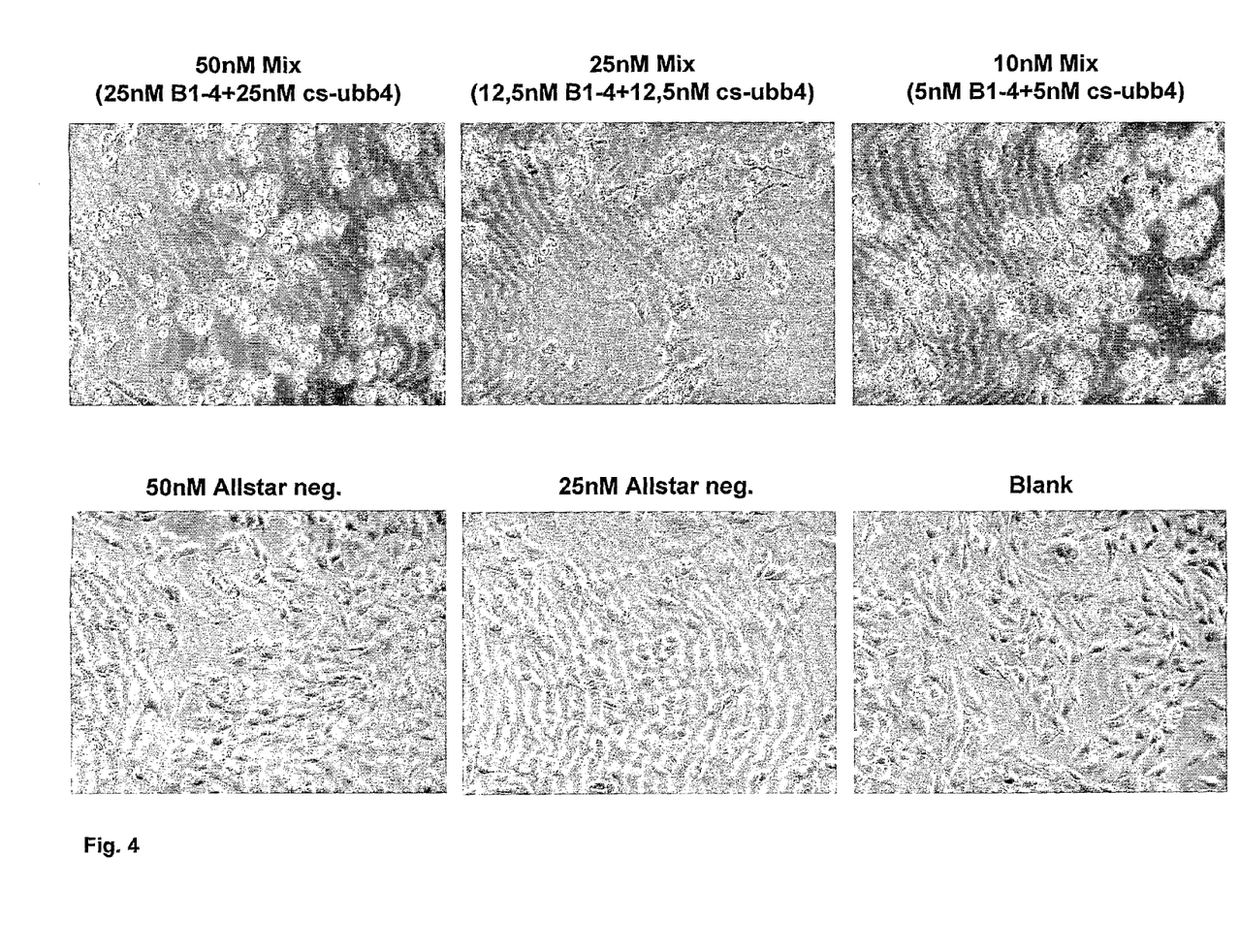
FIG. 4 shows the results of transfection experiments performed in Example 4.

FIG. 4 shows the results obtained with L6 cells upon transfection with the siRNA mixture that was also used in example 2. FIG. 4 shows the results obtained 48 h after transfection.

The invention claimed is:

1. A method for validating an expression modulating analysis or assay using an apoptosis inducing expression modulating compound as a positive control, the method comprising:

introducing the apoptosis inducing expression modulating compound as the positive control into cells of the expression modulating analysis or assay to induce apoptosis in the cells, wherein the apoptosis inducing expression modulating compound is capable of targeting a species specific repetitive element present in untranslated regions of protein coding gene transcripts of more than 50 different genes, wherein the apoptosis inducing expression modulating compound is an RNAi modulating compound that is capable of silencing the expression of the target genes via RNAi, and wherein the RNAi modulating compound has one or more of the following characteristics:
  a) it is a siRNA, miRNA or a shRNA; or
  b) it is expressed by a vector; and
analyzing the cells into which the apoptosis inducing expression modulating compound has been introduced to detect whether apoptosis has been induced in said cells, wherein detection of apoptosis in said cells constitutes the positive control that validates the expression modulating analysis or assay.

2. The method according to claim 1, wherein said apoptosis inducing expression modulating compound is capable of targeting a repetitive element present in 3' UTRs of protein coding gene transcripts.

3. The method according to claim 1, wherein the repetitive element targeted by the expression modulating compound has a length suitable for efficient targeting by RNAi.

4. The method according to claim 1, wherein the species specific repetitive element is a target sequence consisting of:

1727 CCTCCCAAAGTGCTGGGATTA (SEQ. ID No. 1).

5. The method according to claim 1, wherein the cells are analyzed by a microscopic imaging technique or a plate-based imaging technique.

6. The method according to claim 1, wherein the wherein the RNAi modulating compound is a siRNA double-stranded molecule.

7. The method according to claim 6, wherein the siRNA double-stranded molecule has a length of 18 to 30 nt.

8. The method according to claim 1, wherein said apoptosis inducing expression modulating compound is capable of targeting a repetitive element occurring in more than 1000 different genes.

9. The method according to claim 1, wherein said apoptosis inducing expression modulating compound is capable of silencing several different genes by targeting a repetitive element present in 3' UTRs of protein coding gene transcripts.

10. The method according to claim 1, wherein said apoptosis inducing expression modulating compound induces a visible apoptotic phenotype in the transfected cells in less than 72 hours.

11. The method according to claim 1, wherein said apoptosis inducing expression modulating compound is used for transfection in a concentration of at least 5 nM.

12. The method according to claim 1, wherein said apoptosis inducing expression modulating compound is used for transfection in a concentration of at least 10 nM.

13. The method according to claim 1, wherein said apoptosis inducing expression modulating compound is used for transfection in a concentration of at least 25 nM.

14. The method according to claim 1, wherein said apoptosis inducing expression modulating compound is used for transfection in a concentration of at least 50 nM.

15. The method according to claim 1, wherein the repetitive element targeted by the expression modulating compound is an interspersed repetitive element.

16. The method according to claim 1, wherein the repetitive element targeted by the expression modulating compound comprises a sequence conserved enough to select at least 21mers that are of sufficient complementarity to function.

17. The method according to claim 1, wherein the repetitive element targeted by the expression modulating compound is a SINE element.

18. The method according to claim 1, wherein the repetitive element targeted by the expression modulating compound is an Alu sequence.

19. The method according to claim 1, wherein the repetitive element targeted by the expression modulating compound is a B1 repetitive element.

20. The method according to claim 1, wherein the species specific repetitive element is a target sequence consisting of:
1572 CACCTGTAATCCCAGCACTTT (SEQ. ID No. 2).

21. The method according to claim 1, wherein the species specific repetitive element is a target sequence consisting of:
1336 CTGGAGGCTGAGGCAGGAGAA (SEQ. ID No. 3).

22. The method according to claim 1, wherein the species specific repetitive element is a target sequence consisting of:
1278 AAGCCTGTAATCCCAGCACTT (SEQ. ID No. 4).

23. The method according to claim 1, wherein the species specific repetitive element is a target sequence consisting of:
CCTGTAATCCCAGCACTT (SEQ. ID No. 5).

* * * * *